United States Patent [19]

Rutter et al.

[11] 4,190,429

[45] Feb. 26, 1980

[54] CONTROL OF MICROBIAL CONTAMINATION

[75] Inventors: Jerry L. Rutter, Overland Park, Kans.; Janice M. Bergman, Kansas City, Mo.; Kurt J. Bevernitz, Mission, Kans.

[73] Assignee: Gulf Oil Corporation, Pittsburgh, Pa.

[21] Appl. No.: 934,305

[22] Filed: Aug. 17, 1978

[51] Int. Cl.$^2$ ............................................... A01N 9/20
[52] U.S. Cl. ...................................... 71/67; 424/320; 260/561 B
[58] Field of Search ............................ 71/67; 424/320

[56] References Cited

U.S. PATENT DOCUMENTS

| 3,452,082 | 6/1969 | Krimmel | 71/67 X |
| 3,625,985 | 12/1971 | Krimmel | 71/67 X |
| 3,705,194 | 12/1972 | Scherm et al. | 424/320 X |
| 3,962,328 | 6/1976 | Aigami et al. | 424/320 X |

OTHER PUBLICATIONS

Jermyn et al., Chem. Abst., vol. 71 (1969), 77579u.

*Primary Examiner*—Catherine L. Mills
*Attorney, Agent, or Firm*—Donald R. Cassady

[57] ABSTRACT

Microorganisms, as for example, bacteria, fungi, molds and algae, can be inhibited by contact with an effective growth-inhibiting concentration of N-adamantyl gluconamide.

3 Claims, No Drawings

CONTROL OF MICROBIAL CONTAMINATION

BACKGROUND OF THE INVENTION

Gluconic acid is an oxidation product of the monomeric sugar, glucose. It exists to a large extent as the cyclic lactone in aqueous solution.

We have recently found that the hydrazide and lower-alkyl hydrazides of gluconic acid inhibit the growth of microorganisms as for example bacteria, molds, fungi, and algae. The use of these hydrazides has been disclosed in our co-pending patent application Ser. No. 931,236 filed Aug. 7, 1978.

SUMMARY OF THE INVENTION

We have now found that N-adamantyl gluconamide is a growth inhibitor of many microbes which contaminate common laboratory and household apparatus and supplies as for example, work benches, cabinets, bathroom and other sanitary facilities, "clean" rooms and other similar surfaces. The compound is active in aqueous solution at effective inhibitory concentrations of, for example, 0.05 to 0.2 M, against surface contamination.

Surprisingly, the compound also exhibits antimicrobial activity against the usual contaminants in aqueous mixtures as for example, in dispersions, slurries, suspensions, colloidal solutions, and the like. As for example, to control slimes and bacterial, algal, and fungal contamination in holding tanks, ponds, recirculating systems, cutting oils, and the like.

DETAILED DESCRIPTION OF THE INVENTION

The amide of this invention is a stable, organic compound of specific activity as microbial growth inhibitors. The amide exhibits growth inhibitory activity as a chemosterilant when applied to contaminated surfaces and in aqueous mixtures.

The compound is prepared most easily by the reaction of the appropriate adamantyl amine and gluconolactone in a mutual solvent, as for example, ethanol or dimethyformamide. The solid product can be purified by recrystallization from alcohol-ether or alcohol-petroleum ether or similar mixtures of solvents in a manner well known to the art.

In applying the compound to a contaminated surface, the compound can be admixed with detergents, surface active agents, emulsifiers, adjuvants, or other agents commonly found in aqueous cleaning solutions.

EXAMPLE

Gluconolactone, 7.2 g., is dissolved in 200 ml of dimethylformamide and 35 g. of adamantyl amine is added. An exothermic reaction is noted. The resulting amide is isolated by evaporation of the solvent in vacuo and recrystallization of the residue. M.P. 105°–107° C.

Activity of the compound has been observed by testing a 2% aqueous solution of the compound against growing organisms on an agar plate.

Further testing in aqueous systems has been accomplished by adding the compound at 0.05 to 0.2 M concentration to a contaminated aqueous system. Inhibition at 24 and 48 hours was observed in both tests. The compound shows active inhibition against the following microorganisms:

*Enterobacter cloacae*
*Escherchia coli*
*Klebsiella pneumoniae*
*Proteus vulgaris*
*Pseudomonas aeruginosa*
*Salmonella typhimurium*
*Serratia marcescens*
*Staphylococcus aureus*
*Staphylococcus epidermidis*
*Streptococcus pyogenes*
*Trichoderma viride*
*Saccharomyces cerevisiae*
*Dunaliella tertiolecta*

We claim:

1. A method of inhibiting the growth of contaminating microorganisms which comprises contacting the microorganisms with an effective amount of N-adamantyl gluconamide.

2. The method of claim 1 wherein the compound is contacted with the contaminating microorganism on a contaminated surface.

3. The method of claim 1 wherein the inhibition takes place in an aqueous mixture.